US005779869A

United States Patent [19]

Helfer et al.

[11] Patent Number: 5,779,869
[45] Date of Patent: Jul. 14, 1998

[54] LOW FOG ELECTROPHORESIS DEVICE

[75] Inventors: Joel Norman Helfer; Douglas L. Vizard, both of Cheshire, Conn.

[73] Assignee: Eastman Kodak Company, Rochester, N.Y.

[21] Appl. No.: 754,463

[22] Filed: Nov. 22, 1996

Related U.S. Application Data

[63] Continuation of Ser. No. 340,506, Nov. 16, 1994, abandoned, which is a continuation of Ser. No. 250,181, May 27, 1994, abandoned.

[51] Int. Cl.⁶ ..................... C25B 9/00
[52] U.S. Cl. ............ 204/606; 204/456; 204/607; 204/616; 204/621
[58] Field of Search ............ 204/456, 606, 204/607, 616, 621

[56] References Cited

U.S. PATENT DOCUMENTS

| D. 294,859 | 3/1988 | Kreisher et al. | D24/8 |
|---|---|---|---|
| 3,477,950 | 11/1969 | Clement et al. | 210/31 |
| 3,819,505 | 6/1974 | Parent et al. | 204/299 |
| 3,856,656 | 12/1974 | Brink | 204/299 |
| 4,151,065 | 4/1979 | Kaplan et al. | 204/299 R |
| 4,190,517 | 2/1980 | Monthony et al. | 204/299 R |
| 4,234,400 | 11/1980 | Kaplan et al. | 204/180 G |
| 4,552,848 | 11/1985 | Yudelson et al. | 436/86 |
| 4,576,693 | 3/1986 | Kreisher et al. | 204/180.1 |
| 4,576,702 | 3/1986 | Peck et al. | 204/299 R |
| 4,576,703 | 3/1986 | Peck et al. | 204/299 R |
| 4,588,491 | 5/1986 | Kreisher et al. | 204/299 R |
| 4,589,965 | 5/1986 | Kreisher | 204/182.8 |
| 4,622,124 | 11/1986 | Kriesher et al. | 204/301 |
| 4,672,043 | 6/1987 | Yudelson | 436/86 |
| 4,800,010 | 1/1989 | Hellman, Jr. | 204/299 R |
| 4,802,969 | 2/1989 | Hellman, Jr. | 204/299 R |
| 4,828,669 | 5/1989 | Hellman, Jr. | 204/299 R |
| 4,865,715 | 9/1989 | Hellman, Jr. | 204/299 R |
| 4,911,816 | 3/1990 | Love et al. | 204/299 R |
| 4,944,483 | 7/1990 | Nishizawa | 249/83 |
| 4,948,480 | 8/1990 | Christy, Jr. et al. | 204/182.8 |
| 4,959,133 | 9/1990 | Adcock | 204/182.8 |
| 4,975,170 | 12/1990 | Hellman, Jr. | 204/299 R |
| 5,027,018 | 6/1991 | Kindlmann et al. | 307/571 |
| 5,043,051 | 8/1991 | Berry et al. | 204/299 R |
| 5,047,322 | 9/1991 | Emmons et al. | 435/6 |
| 5,066,376 | 11/1991 | Osterhoudt et al. | 204/182.8 |
| 5,073,603 | 12/1991 | Ponticello | 525/350 |
| 5,149,416 | 9/1992 | Osterhoudt et al. | 204/299 |
| 5,212,253 | 5/1993 | Ponticello et al. | 525/328 |
| 5,350,552 | 9/1994 | Ebata et al. | 204/299 R |

FOREIGN PATENT DOCUMENTS 0300924  1/1989  European Pat. Off. .

Primary Examiner—Cecilia J. Tsang
Assistant Examiner—C. Delacroix-Muirheid
Attorney, Agent, or Firm—Doreen M. Wells

[57] ABSTRACT

An electrophoresis device consists of a housing which has opening(s) for the movement of gases from inside the housing to outside the housing and opening(s) for the movement of gases from outside the housing to inside the housing, whereby the condensation of gases on the inside of the housing is avoided or minimized.

9 Claims, 2 Drawing Sheets

LOW FOG ELECTROPHORESIS DEVICE

CROSS-REFERENCE TO RELATED APPLICATION

This is a continuation of U.S. application Ser. No. 08/340,506, filed 16 Nov. 1994, now abandoned, which is a continuation of U.S. application Ser. No. 08/250,181, filed 27 May 1994, now abandoned.

FIELD OF INVENTION

This invention relates to an electrophoresis device. More specifically this invention relates to a low fog electrophoresis device.

BACKGROUND OF THE INVENTION

A great number of electrophoresis devices exist which take advantage of the principle that charged particles suspended between poles of an electric field tend to migrate toward the pole whose charge is opposite to that of a given particle. Most electrophoresis devices consist of a housing which encloses two electrodes and a separating medium, such as a gel matrix, in a buffer solution. The housing usually consists of a horizontal box-shaped or cylindrical-shaped base which is open on the top and a cover which fits over the base providing an air-tight housing. In use, as electrophoresis progresses, the high voltages across the gel matrix and the buffer solution cause volatiles, vapors, and steam, collectively referred to as gases, to evolve from the buffer solution and the gel matrix. Some of the gases condense on the inside cover of the electrophoresis device making it difficult for the operator of the electrophoresis device to watch the progress of the electrophoresis procedure.

Therefore, there is a need for an electrophoresis device which eliminates or minimizes the condensation of gases on the inside housing of the electrophoresis device, thereby making it possible for the operator to easily watch the progress of electrophoresis experiments.

SUMMARY OF THE INVENTION

This invention provides an electrophoresis device consisting of a housing, an electrophoresis chamber enclosed by the housing, and a plurality of electrodes located in the electrophoresis chamber. The housing has an inlet portion having an inlet, and an outlet portion having an outlet. The inlet of said inlet portion and the outlet of said outlet portion provide for the communication of gases into and out of the electrophoresis chamber. The inlet consists of one or more openings. The outlet consists of one or more openings. The opening or openings for the inlet and outlet are preferably separate. Additionally, the outlet portion is preferably located above the inlet portion on the electrophoresis housing. Further, the communication of gases into and out of the electrophoresis chamber preferably occurs simultaneously.

This invention also provides a method for minimizing the condensation of gases on the inside of an electrophoresis device during an electrophoresis experiment which comprises providing an electrophoresis device comprising a housing which encloses an electrophoresis chamber containing a plurality of electrodes, introducing a gel matrix into said chamber, introducing a buffer solution into said chamber to a level above the level of the gel matrix, adding to one end of the gel matrix an electrophoresis experiment sample, completing an electrical circuit including said electrodes to start the electrophoresis experiment, thereby causing gases to evolve from the buffer solution, providing an exit for hot evolved gases from the electrophoresis chamber, providing an inlet for gases into said chamber and thereby drawing colder and drier air or gases from outside into the electrophoresis chamber to minimize the condensation of gases and make it possible for an operator to watch the progress of the electrophoresis experiment.

Therefore, this invention provides a low fog electrophoresis device. The inlet and outlet in the electrophoresis device housing provide for the circulation of gases from inside the housing to outside the housing and drier air from outside the housing to inside the housing. This circulation of gases eliminates or minimizes the condensation of the gases on the inside of the housing of the electrophoresis device making it possible for an operator to watch the progress of electrophoresis experiments. Additionally, the circulation of gases provides a mechanism to cool the separating medium.

Other advantageous features will become apparent upon reference to the attached drawings, when read in light of the Description of the Preferred Embodiments.

DESCRIPTION OF THE PREFERRED EMBODIMENTS

In the following description, the invention is described in connection with a preferred embodiment, in which the housing of the electrophoresis device has a horizontal configuration including a trapezoidal-shaped cover and base, and multiple openings in both the inlet portion and the outlet portion to allow the movement of gases from and into the housing. However, the invention is useful if the electrophoresis device has altered configurations, for example a vertical configuration.

The "inlet portion" is defined as the part of the electrophoresis housing surrounding the inlet for the movement of gases into the electrophoresis housing. The "inlet" refers to the one or more openings in the inlet portion. The "outlet portion" is defined as the part of the electrophoresis housing surrounding the outlet for the movement of gases out of the electrophoresis housing. The "outlet" refers to the one or more openings in the outlet portion.

Figure 1:
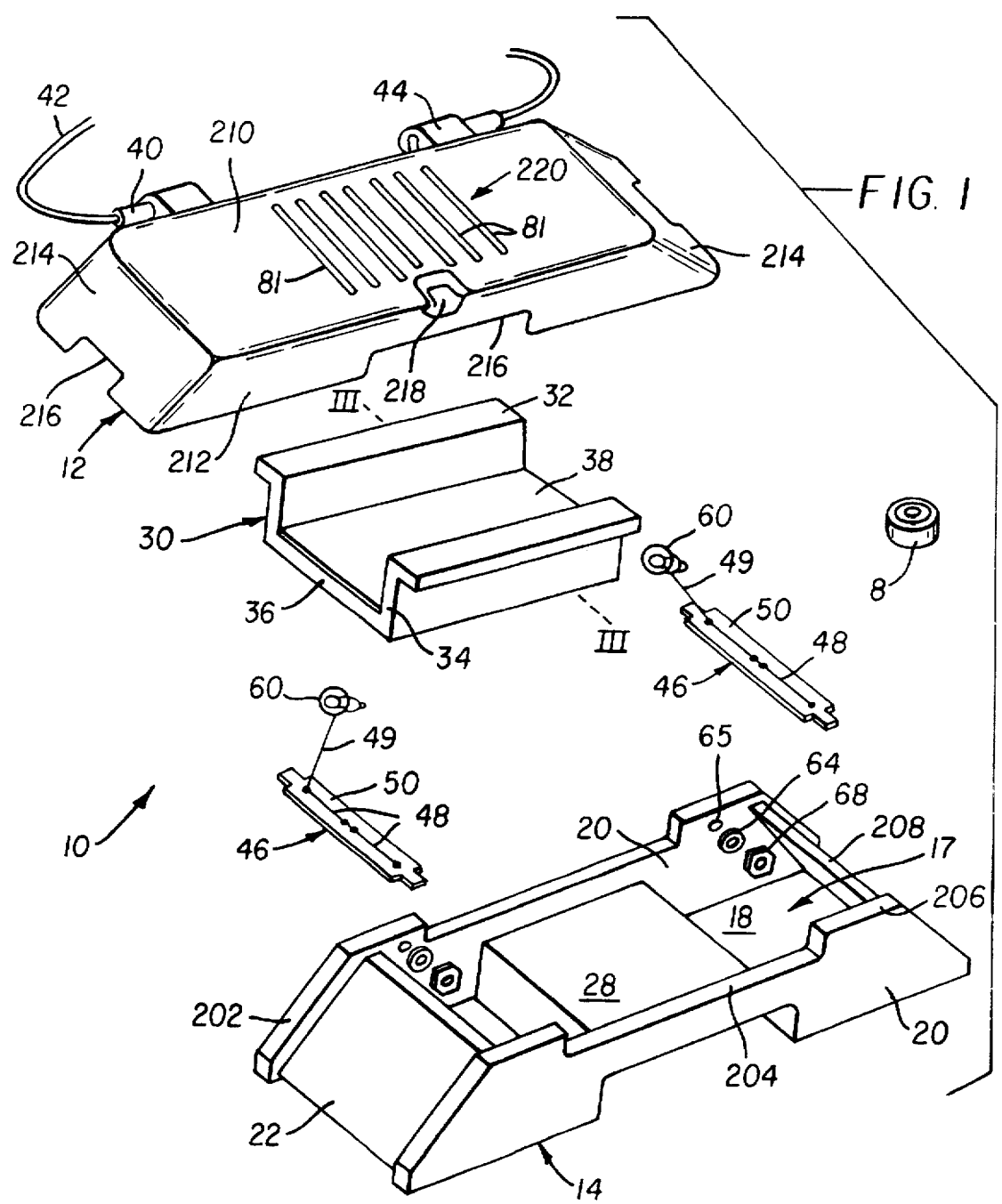
FIG. 1 is an exploded view of an electrophoresis device of the invention.
Figure 2:
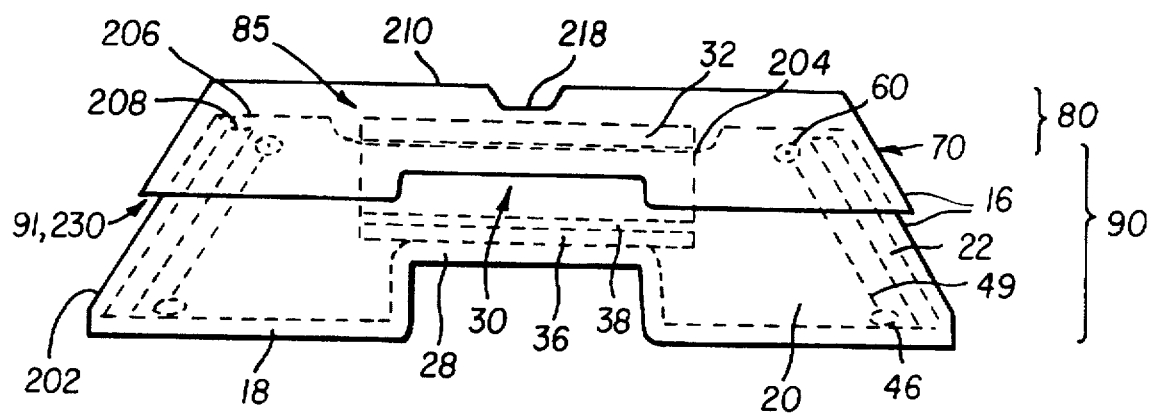
FIG. 2 is a side view of the electrophoresis device shown in FIG. 1.

An electrophoresis device 10 of the invention shown in FIGS. 1 and 2 consists of a cover 12 and a base 14. The cover 12 and the base 14 can be made of transparent material. Together the cover 12 and the base 14 make up the housing 16. The housing 16 is electrically insulating. The cover 12 is disposed on base 14 in roughly the same manner as a roof on a house. The overall shape of cover 12 and base 14 is not critical to the practice of the invention; however, a preferred overall shape will be described herein. The base 14 is constructed to form a water-tight buffer solution compartment 17 as defined by a bottom wall 18, side walls 20 and end walls 22. The uppermost surface area of the buffer solution compartment is defined as the uppermost surface area of the buffer solution when the compartment 17 is filled with buffer solution. A fill level 70 for the buffer solution is indicated in FIG. 2. Bottom wall 18 includes a step-up bridge 28. When not in use, step-up bridge forms a convenient hand grip for transporting the electrophoresis device 10.

In this embodiment, side walls 20 each have inwardly sloped end margins 202 and an upper margin 206 that includes a central notch 204. End walls 22 extend between side walls 20 at opposite ends of base 14. End walls 22 are each inset from adjoining end margins 202 of side walls 20 and have substantially the same slope as respective end margins 202. End walls 22 each terminate at an upper end 208 that is lower than adjoining portions of upper margin 206 of side walls 20.

Electrode units 46 consist of metal wires 48, preferably platinum wires, which are exposed and held on mounting members 50 and placed in the opposite bottom corners of compartment 17 of electrophoresis device 10. Insulated conductors 49 join wires 48 to electrical connectors 60. Electrical connectors 60 are removably attached to the base 14 through holes 65. Rubber washers 64 help to protect the electrical connection between the electrical connectors 60 and the insulated conductors 49 from the buffer solution when it fills the compartment 17. Plastic nuts 68 capture and retain the washers 64 and the end of the wires 48.

Figure 3:
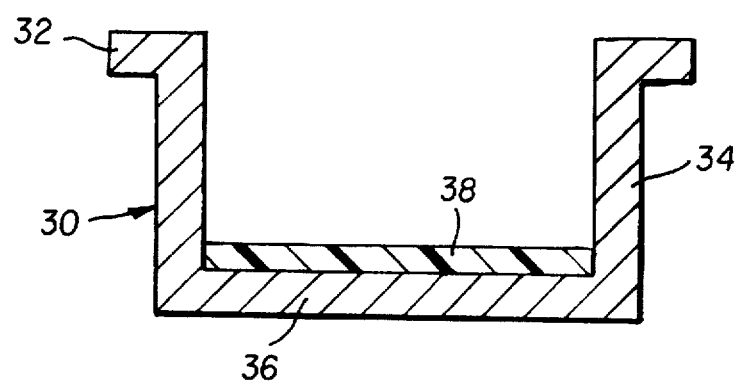
FIG. 3 is a cross-sectional view of the tray of the electrophoresis device shown in FIG. 1, taken substantially along the line III—III of FIG. 1.

Referring now to FIGS. 1, 2 and 3, a tray 30 is in place in housing 16. Tray 30 has wings 32 which rest in notches 204 of side walls 20. Wings 32 have a width approximately equal to the thickness of side walls 20. Tray 30 also has side members 34 and a bottom member 36. The bottom member 36 rests on the step-up bridge 28. The gel matrix 38 rests on the bottom member 36 of tray 30. The gel matrix can be formed on the bottom member 36 by any method known in the art. For example, one known method is to use a casting fixture and a comb-shaped device to provide holes in the gel for receiving the sample(s).

The cover 12 has a top 210 which is formed to opposed sides 212 and opposed ends 214. Top 210 is preferably flat. Sides 212 and ends 214 each include a notch 216. Cover 12 is longer and wider than the base 14. Top 210 includes a series of parallel slots 81 which are referred to collectively as outlet 220.

An outside electrical source is attached via insulated conductors 42 with cylindrical molded ends 40 which removably plug into receivers 44 on cover 12. Electrical connectors 60 contact receivers 44 only when the cover 12 is properly positioned onto the base 14 this position of the cover and base will be referred to herein as the "operative position." When the cover 12 and the base 14 are in the operative position, electric current from the electrical source flows into and out of the electrophoresis device 10. The operative position of the base 14 and the cover 12 is shown in FIG. 2. The preferred embodiments for the receivers 44 and the connectors 60 are described in Helfer, U.S. Pat. No. 5,405,520, filed Jan. 27, 1994, assigned to the Eastman Kodak Co., which is incorporated herein by reference.

Unless otherwise indicated this paragraph describes the electrophoresis device when the cover 12 and the base 14 are in the operative position as shown in FIG. 2. Cover 12 is supported by the receivers 44 which rest on the electrical connectors 60 and by a cover support 218 which rests on one of the wings 32 of the tray 30. The cover support 218 is a molded notch in the top 210 of cover 12. Top 210 of cover 12 is substantially parallel to step-up bridge 28. Sides 212 and ends 214 of the cover 12 are parallel to respective side walls 20 and end walls 22 of the base 14. Top 210 is spaced apart from upper ends 206 of side walls 20 and upper ends 208 of end walls 22. An electrophoresis chamber 85 is the area inside the cover 12 and the base 14. The electrophoresis chamber 85 includes the buffer solution compartment 17 and the area above the compartment 17 and under the cover 12. Because the sides 212 and ends 214 of the cover 12 are longer and wider than the side walls 20 and the end walls 22 of the base 14, inlet openings 91 are defined by the cover 12 and the base 14. The ends 214 of cover 12 and end walls 22 of base 14 define a pair of opposed inlet openings 91, and the sides 212 of the cover 12 and the side walls 20 define another pair of opposed inlet openings 91. The inlet openings 91 collectively make up the inlet 230. The inlet 230 provides for the movement of gases into the electrophoresis chamber 85 from outside the electrophoresis housing 16.

The housing 16 has an outlet portion 80 and an inlet portion 90. The outlet portion 80 in this embodiment is the cover 12 which has parallel slots 81 in it. The inlet portion 90 consists of the cover 12 and the base 10 which define multiple openings 91 when the cover 12 and the base 10 are in the operative position.

The outlet 220 and the inlet 230 can be made in any shape or size and can be located only on the cover 12 and/or only on the base 14 as long as the gases can enter and exit the electrophoresis device. One opening could even serve as the inlet and the outlet. However, it is preferred that the opening or openings which provide direct access to electrical parts not have a thickness greater than 3 mm, because this is the maximum space allowable for access to uninsulated electrical parts as established by the Electrical Safety Code for Hospital and Laboratory Equipment ESCHLE (1983). In other words, in this embodiment the openings 81 on the cover 12 can be any shape as long as a test probe having a diameter of greater than 3 mm is excluded from the openings 81.

The optimum number of openings 81, 91 for the outlet and inlet will depend on the area of each opening. In the embodiment described herein, the area of the openings 81 for the outlet 220 is related to the size of the top 210 of the cover 12. The area of the outlet 220 is preferably 1 to 75 percent, more preferably 3 to 30 percent and most preferably 4 to 7 percent of the area of the top 210. The area of the inlet 230 is at least equal to the area of the outlet 220, more preferably the inlet 230 has an area at least 20 percent greater than the outlet 220. The area of the outlet 220 may be related to the uppermost surface area of the buffer solution compartment which is the uppermost surface area of the buffer solution when the buffer solution compartment 17 is filled with buffer solution. The area of the outlet 220 is preferably 1 to 75 percent, more preferably 3 to 30 percent and most preferably 4 to 7 percent of the uppermost surface area of the buffer solution compartment. Again, the area of the inlet 230 is at least equivalent to the area of the outlet 220, more preferably the inlet 230 has an area at least 20 percent greater than the outlet 220.

For best results, the electrophoresis device 10 should be level when in use. To check if the electrophoresis device 10 is level, a removable leveling bubble 8 is supplied. Alternately, the leveling bubble could be permanently attached to the housing 16. Prior to use the leveling bubble 8 is placed onto the tray 30 when the tray 30 is in the electrophoresis device 10 and the electrophoresis device 10 is leveled. Once the electrophoresis device 10 is level, the removable leveling bubble 8 should be removed from the electrophoresis device 10 prior to use. To perform an electrophoresis experiment, the tray 30 is placed on the step-up bridge 28, and buffer solution is added to compartment 17 to a level that is above the level of the gel matrix 38, for example, to fill level 70. Then, a sample is prepared and added, usually by pipette to one end of the gel matrix 38 on the tray 30. Next, the cover 12 is placed onto the base 14 in the operative position which completes the electrical circuit and therefore starts the electrophoresis experiment. During the experiment gases evolve from the buffer solution. These gases exit the electrophoresis chamber 85 through the outlet 220 in the outlet portion 80 and drier gases from outside the electrophoresis device 10 enter the electrophoresis chamber 85 through the inlet 230 in the inlet portion 90 of the electrophoresis device 10. This movement of gases prevents the fogging of the electrophoresis device and provides a mechanism to cool the separating medium.

Although not wishing to be bound by theory, it is believed that the communication of gases into and out of the electrophoresis chamber occurs by convection, that is, hot gases evolved from the buffer solution rise and exit the electrophoresis chamber 85 through the slots 81 in the outlet portion 80 while colder, drier air or gases are drawn into the electrophoresis chamber 85 through opening(s) 91 in the inlet portion 90.

The invention has been described in detail with particular reference to preferred embodiments thereof, but it will be understood that variations and modifications can be effected within the spirit and scope of the invention.

PARTS LIST 10 electrophoresis device
12 cover
14 base
16 housing (base and cover)
17 buffer solution compartment
18 bottom wall of base
20 side walls of base
22 end walls of base
28 step-up bridge (part of bottom wall)
38 gel matrix
30 tray
32 wings of tray
34 sides of tray
36 bottom of tray
46 electrode units
48 wire on electrode units
50 mounting members of electrode units
42,49 insulated conductors
60 electrical connectors
64 rubber washers
68 plastic nuts
40 cylindrical molded ends
44 receivers
8 leveler
80 outlet portion
90 inlet portion
81 opening in outlet portion
91 openings in inlet portion
85 electrophoresis chamber
202 end margins of side walls of base
206 upper margins of side walls of base
204 central notch of upper margin of side walls of base
208 upper end of end walls of base
65 holes in base
210 top of cover
212 sides of cover
214 ends of cover
220 outlet
230 inlet
216 notches in cover
218 cover support
70 fill level

What is claimed is:

1. An electrophoresis device comprising:
a housing comprising an inlet portion having an inlet, and an outlet portion having an outlet, said outlet portion being located above said inlet portion; a buffer solution compartment within said housing having a fill level for buffer solution; and a plurality of electrodes located in said buffer solution compartment; wherein openings of the inlet and outlet into the electrophoresis device are located above said fill level for the buffer solution.

2. A device as defined in claim 1, further comprising a step-up bridge and wherein said housing further comprises a cover and a base, wherein said cover comprises said outlet portion.

3. A device as defined in claim 2, wherein said outlet portion comprises at least one opening and a test probe having a diameter of 3 mm is excluded from each said opening of said outlet portion.

4. A device as defined in claim 3, wherein said cover is removably mounted on said base and said cover further comprises a top.

5. A device as defined in claim 4, wherein the area of said outlet comprises 1 to 75 percent of the surface area of said top.

6. A device as defined in claim 3, wherein the area of said inlet is at least equivalent to the area of said outlet.

7. A device as defined in claim 6, wherein the area of said outlet further comprises 3 to 30 percent of the surface area of said top.

8. An electrophoresis device comprising
an electrically insulating housing having a base and a removable transparent cover resting on said base in an operative position to define an electrophoresis chamber, said base having a bottom wall, side walls and end walls that define a water-tight compartment for buffer solution within said chamber, said bottom wall having a step-up bridge within said water-tight compartment,
a removable gel matrix tray having side members and a bottom member, a gel matrix formed on the upper surface of said bottom member and the lower surface of said bottom member resting on said step-up bridge,
electrode units positioned in opposite bottom corners of the water-tight compartment of said base, means connecting said electrode units with an outside electrical source when said cover rests on said base in said operative position,
said cover having depending sides and ends that are longer and wider than the side walls and end walls of said base, the ends of said cover and the end walls of said base thereby defining a pair of opposed inlet openings adapted to admit gases or air from outside into the electrophoresis chamber, and
outlet means in said cover for allowing gases evolved from the buffer solution to exit the electrophoresis chamber.

9. A method for minimizing the condensation of gases on the inside of an electrophoresis device during an electrophoresis experiment which comprises
providing an electrophoresis device comprising a housing which encloses an electrophoresis chamber containing a plurality of electrodes,
introducing a gel matrix into said chamber,
introducing a buffer solution into said chamber to a level above the level of the gel matrix, adding to one end of the gel matrix an electrophoresis experiment sample, completing an electrical circuit including said electrodes to start the electrophoresis experiment, thereby causing gases to evolve from the buffer solution, providing an exit for hot evolved gases from the electrophoresis chamber, providing an inlet for gases into said chamber and thereby drawing colder and drier air or gases from outside into the electrophoresis chamber to minimize the condensation of gases and make it possible for an operator to watch the progress of the electrophoresis experiment.

* * * * *